United States Patent [19]

McMillan

[11] Patent Number: 5,336,597
[45] Date of Patent: * Aug. 9, 1994

[54] CELL SURFACE ANTIGEN DETECTION METHOD

[75] Inventor: Robert McMillan, Del Mar, Calif.

[73] Assignee: The Scripps Research Institute, La Jolla, Calif.

[*] Notice: The portion of the term of this patent subsequent to Mar. 7, 2006 has been disclaimed.

[21] Appl. No.: 967,449

[22] Filed: Oct. 28, 1992

Related U.S. Application Data

[63] Continuation of Ser. No. 124,905, Nov. 24, 1987, Pat. No. 5,176,998, which is a continuation-in-part of Ser. No. 936,125, Dec. 1, 1986, Pat. No. 4,810,632.

[51] Int. Cl.$^5$ ............... G01N 33/538; G01N 33/543; G01N 33/564
[52] U.S. Cl. ............ 435/7.2; 435/7.21; 435/7.24; 436/506; 436/507; 436/518; 436/541
[58] Field of Search ............ 435/7.2, 7.21, 7.24; 436/506, 507, 518, 541

[56] References Cited

U.S. PATENT DOCUMENTS

| | | | |
|---|---|---|---|
| 4,342,566 | 8/1982 | Theofilopoulos et al. | 435/7 |
| 4,443,427 | 4/1984 | Reinherz et al. | 424/1.1 |
| 4,643,971 | 2/1987 | Fradet et al. | 435/240 |
| 4,670,394 | 6/1987 | Pollard et al. | 435/240.21 |
| 4,690,907 | 9/1987 | Hibino et al. | 436/514 |
| 4,695,538 | 9/1987 | Cote et al. | 435/240 |
| 4,810,632 | 3/1989 | McMillan | 435/7.2 |
| 5,176,998 | 1/1993 | McMillan | 435/7.2 |

FOREIGN PATENT DOCUMENTS 0169729  1/1986  European Pat. Off. .

OTHER PUBLICATIONS

E. T. Maggio, ed., "Enzyme-Immunoasssay", CRC Press, Inc., Boca Raton, Fla. (1980) pp. 175–176.
Nisonoff, in "Introduction to Molecular Immunology", Sinauer Associates, Inc., Sunderland, Mass. (1982) pp. 152–153.
"Alternative Immunoassays", W. P. Collins, ed., John Wiley & Sons, New York, N.Y. (1985) pp. 83–84.
Jerne, Ann. Immunol. 125: 373–389 (1974).
Woods, et al., Blood 63(2): 368–375 (1984).
Woods, et al., Blood 64(1): 156–160 (1984).
Millard, et al., Blood 70: 1495–1499 (1987).
Tamerius, et al., Blood 62: 744–749 (1983).
McMillan, et al., Thrombosis and Haemostasis 58: 530, No. 1937 (1987).
McMillan, et al., Chem. Abstracts 97(7): 464–465, Abstract No. 53671d (1982).

Primary Examiner—David Saunders
Attorney, Agent, or Firm—Douglas A. Bingham; Thomas Fitting; April C. Logan

[57] ABSTRACT

The present invention provides a method for assaying a sample of cells for the presence of a cell surface antigen. More particularly, the present invention describes methods for detecting the presence of plasma and cell bound autoantibodies against cell surface antigens. In addition, the present invention provides a method of crossmatching donor platelets and transfusion recipients.

6 Claims, No Drawings

CELL SURFACE ANTIGEN DETECTION METHOD

This invention was made with the support of the Government of the United States of America. The government may have certain rights in the invention.

This is a continuation of copending U.S. application Ser. No. 124,905 filed on Nov. 24, 1987, now U.S. Pat. No. 5,176,998, which is a continuation-in-part of copending U.S. application Ser. No. 936,125 filed on Dec. 1, 1986 now U.S. Pat. No. 4,810,632.

DESCRIPTION

1. Technical Field

The present invention relates to immunological methods for determining platelet histocompatibility type and for characterizing the anti-platelet immune status of an individual.

2. Background.

The platelet histocompatibility type and anti-platelet immune status of an individual both play important roles in the management of clinical conditions due to anti-platelet immune response. Anti-platelet immune responses resulting in the production of platelet-destroying antibodies occur as a result of, among other things, pregnancy, platelet transfusion therapy and anti-platelet autoimmune disease.

Of particular interest to the present invention is platelet transfusion therapy. Since its beginning over three-quarters of a century ago, platelet transfusion therapy has played an increasingly important role in the supportive care of patients with bone marrow failure. However, one impediment to progress in this field has been the finding that a significant proportion of recipients become refractory to repeated transfusions from random donors. Platelet rejection appears to be due in many cases to anti-platelet antibodies in the transfusion recipient (donee) induced as a result of alloimmunization.

Alloimmunization is the process wherein an individual produces antibodies in response to exposure to an alloantigen. An alloantigen is an antigen, typically a protein, that exists in alternative (allelic) forms in different individuals of the same species, and thus induces an immune response when one form is transferred (as by transfusion or tissue graft) to members of the same species who have not previously been exposed to it. Class I human leukocyte antigens (HLA) are one group of alloantigens that are found on the surface of platelets and are capable of inducing alloantibodies (antibodies against alloantigens) that mediate platelet rejection in transfusion recipients. Yankee et al. first demonstrated that transfusions of HLA-matched platelets from single donors frequently results in good increments in platelet count in transfusion recipients. That is, crossmatching of donor platelet and recipient HLA type has been found to reduce platelet rejection in transfusion recipients.

Unfortunately, HLA matched platelet donors are available for only a minority of alloimmunized patients, and the response of recipients to partially matched donor platelets is less predictable. The recognition of cross-reacting groups and the differential expression of certain HLA antigens (e.g., B12) on platelets has facilitated educated guessing during donor selection. However, a means of selecting donor platelets without resorting to trial and error would be advantageous.

Characterization of an individual's anti-platelet immune status is, as previously mentioned, also important in managing autoimmune diseases. One such disease is chronic immune thrombocytopenic purpura (ITP), a syndrome of destructive thrombocytopenia due to an antibody against a platelet-associated antigen (McMillan, N. Engl. J. Med. 304:1135–1147 (1981), and Kelton et al Semin. Thromb. Haemost., 8:83–104 (1982). van Leeuwen et al., (Blood, 59:23–26 (1982)) first provided evidence that autoantibodies were present in some ITP patients. They noted that of 42 antibody eluates from ITP platelets, 32 would bind to normal but not to thrombasthenic platelets; the remaining eluates bound to both. Since thrombasthenic platelets are deficient in platelet glycoproteins (GP) IIb and IIIa, they suggested that these ITP patients had autoantibodies to one of these glycoproteins.

Direct evidence for anti-glycoprotein autoantibodies in chronic ITP has been provided by subsequent studies using a variety of methods. Woods et al. showed binding of autoantibodies from ITP patients to the GPIIb-/IIIa complex or to GPIb attached to microtiter wells with monoclonal antibodies and confirmed these observations by immunoprecipitation. See Woods et al., Blood, 63:368–375 (1984) and Woods et al., Blood, 64:156–160 (1984). Using the former method, they noted anti-GPIIb/IIIa or anti-GPIb autoantibodies in about 10% of patients, much less than the percentage observed by the indirect studies of van Leeuven et al. supra.

Other investigators also detected antiplatelet autoantibodies in chronic ITP patients using immunoblotting (Mason et al., Br. J. Haematol., 56:529–534 (1984) and Beardsley et al., J. Clin. Invest. 74:1701–1707 (1984)), immunoprecipitation, (Woods et al., Blood, 63:368–375 (1984), Woods et al., Blood, 64:156–160 (1984) and Devine et al., Blood, 64:1240–1245 (1984)), inhibition of murine monoclonal anti-GPIIb/IIIa antibody binding to ITP platelets (Varon et al., Proc. Natl. Acad. Sci. USA, 80:6992–6995 (1983)) and crossed immunoelectrophoresis (Szatkowski et al., Blood, 67:310–315 (1986)). Nugent et al. ("Proceedings of the INSERM Symposium on utilization of monoclonal antibodies for the understanding and detection of platelet activity." Amsterdam, Elsevier Science Publishers, 1986) and Asano et al., (Blood, 66:1254–1260 (1985)) have established human hybridomas from ITP lymphocytes which synthesize monoclonal antiplatelet antibodies. Some of these are specific for platelet glycoproteins (Nugent et al., supra).

Of the assays used for demonstrating antiglycoprotein autoantibodies in chronic ITP, the microtiter well assay (Woods et al., Blood, 63:368–375 (1984) and Woods et al., Blood, 64:156–160 (1984)) is most easily adaptable to clinical use. However, the low percentage of positive tests (about 10%) when compared to that of van Leeuwen et al. (about 76%) suggested that solubilization of the platelets prior to antibody sensitization may alter some of the epitopes. For this reason, an assay (immunobead assay) for antiglycoprotein autoantibodies was designed where platelets are sensitized prior to their solubilization to take advantage of the possibility that the epitopes expressed by the platelet surface antigens may remain more stable when bound to antibody. This assay can measure both platelet-associated and plasma autoantibodies.

BRIEF SUMMARY OF THE INVENTION

The present invention provides a method of assaying a sample of cells for the presence of a cell surface antigen, which method comprises the steps of:

(a) admixing said cells with an antibody capable of immunoreacting with said antigen to form a cell-sensitizing reaction admixture, (b) maintaining said cell-sensitizing reaction admixture for a time period sufficient to form an immunocomplex containing said antigen and said antibody, thereby forming sensitized cells, (c) lysing said sensitized cells to provide an aqueous composition, said composition containing solubilized immunocomplex when said immunocomplex is formed in step (b), (d) admixing said aqueous composition with a solid support capable of specifically binding said immunocomplex, thereby forming a solid/liquid phase admixture, (e) maintaining said solid/liquid phase admixture for a time period sufficient for any of said immunocomplex present to bind to said solid support, thereby forming a solid-phase bound complex, and (f) assaying for the presence of any bound complex that formed in step (e).

The present invention also provides a method for detecting the presence of a cell surface antigen, which method comprises the steps of:

(a) providing an aliquot of cells to be assayed, any cells of said aliquot bearing the surface antigen to be detected having an immunocomplex containing an antibody to said antigen immunoreacted with said antigen;

(b) lysing the cells of said aliquot to provide cellular debris, and when said immunocomplex was present in the aliquot, a solublized immunocomplex; and (c) assaying from the presence of said solubilized immunocomplex.

In another embodiment, the present invention contemplates a method of assaying platelet compatibility between donor and patient, which method comprises the steps of:

(a) admixing an aliquot of serum or plasma from a patient with platelets of a prospective donor to form an aqueous, liquid admixture;

(b) maintaining said admixture under biological assay conditions for a predetermined time period sufficient for any alloantibodies present in the serum or plasma to immunoreact with a platelet antigen to form an immunocommplex;

(c) lysing the platelets of said admixture to form cellular debris and a solublized immunocomplex when said alloantibodies and said platelet antigen were present in said admixture; and (d) assaying for the presence of said immunocomplex.

Also contemplated by the present invention is a method of typing cells for the presence of a group of cell surface antigens, which method comprises the steps of:

(a) reacting an aliquot of a cell sample to be typed with an antibody that reacts with an antigen epitope common to substantially all of the group of the cell surface antigens sought to form an immunocomplex;

(b) lysing the cells of said sample to provide cellular debris and a solublized immunocomplex;

(c) reacting the solubilized imanunocomplex with indicating paratopic molecules that immunoreact with at least one specific cell surface antigen epitope of the group of cell surface antigens to form a second immunocomplex; and (d) assaying for the presence of said second immunocomplex.

DETAILED DESCRIPTION OF THE INVENTION

I. Definitions

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab' F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The phrase "monoclonal antibody." in its various grammatical forms refers to a population of one species of antibody molecule of determined (known) antigen-specificity. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each inunospecific for a different antigen.

As used herein, the term "biological assay conditions" is used for those conditions wherein a molecule useful in this invention such as an antibody binds to another useful molecule such as an antigen epitope within a pH value range of about 5 to about 9, at ionic strengths such as that of distilled water to that of about one molar sodium chloride, and at temperatures of about 4 degrees C. to about 45 degrees C.

The word "complex" as used herein refers to the product of a specific binding agent-ligand reaction. An exemplary complex is an immunoreaction product formed by an antibody-antigen reaction.

A "specific binding agent" is a molecular entity capable of selectively binding another molecular entity or ligand. Exemplary specific binding agents are paratopic molecules, complement proteins or fragments thereof, S. aureus protein A, and the like. Preferably, the specific binding agent binds its ligand when the ligand is present as part of a complex.

II. Assay Methods

The present invention broadly contemplates a method of detecting the presence of a cell surface antigen. In accordance with this method, cells to be assayed, typically blood cells, are admixed with an antibody capable of immunoreacting with the antigen while it is present on the cell surface. The resulting admixture is a first immunoreaction admixture and it is typically referred to as a cell-sensitizing reaction admixture because it produces "antibody-sensitized" cells.

Cell surface antigens known to be clinically useful markers whose presence can be determined by a method of the present invention include those that determine histocompatibility, such as a major histocompatibility complex (MHC) antigen, particularly a human leukocyte antigen (HLA). Useful cell surface antigens also include glycoproteins (GP) that comprise membrane associated receptors that bind Arg-Gly-Asp-containing proteins. Such glycoproteins include GPIb, GPIIb, GPIIIa and the cell surface complexes containing those proteins, such as the GPIIb/IIIa complex.

Antibodies capable of immunoreacting with antigens on the surface of cells are well known and include those that are available from the American Type Culture Collection (ATCC), Rockville, Md.

The cell-sensitizing reaction admixture is maintained for a time period sufficient for an immunocomplex containing the antibody and the cell surface antigen to form on the cellular surface. As is well known, the time period required for immunocomplex formation depends on a variety of factors including temperature and concentration of reactants. Typically, the time period is predetermined for a given set of reaction conditions by well known methods prior to performing the assay. Under biological assay conditions, the maintenance time period is usually from minutes to hours such as 30 minutes to about 2 hours.

Maintaining the cell-sensitizing reaction for a time sufficient for immunocomplex formation results in the production of antibody-sensitized cells which are typically separated by washing and centrifugation from any non-immunoreacted antibody. If the cells have the cell surface antigen being assayed for, the sensitized cells will have a cell surface associated immunocomplex.

To determine the presence of any cell surface immunocomplex formed, the sensitized cells are lysed to produce an aqueous composition containing solubilized cell surface protein. Lysing can be accomplished by admixing the sensitized cells with an aqueous buffer such as water or saline and a surfactant capable of solubilizing cell surface protein. Surfactants capable of solubilizing cell surface proteins include detergents such as polyoxyethylene (9) octyl phenyl ether, available under the trademark Triton X-100 from Rohm and Hass Co., Inc., Philadelphia, Pa.

The lysing reaction admixture formed upon admixture of the cells and surfactant is maintained for a time period sufficient for the surfactant to solubilize (dissociate from the cell membrane) surface protein of the cells, including any cell surface immunocomplex formed. Typically, the time period used for solubilization is predetermined and usually is in the range of from minutes to hours such as about 15 minutes to about 2 hours.

Methods for detecting solubilization of cell surface protein are well known and include using immunological methods to monitor the aqueous phase of the lysing reaction admixture for appearance of a protein known to be associated with the surface of the cells being assayed. For instance, the glycoproteins IIb and IIIa are found associated with the surface of all normal platelets and can be used as immunological markers of surface protein solubilization when platelets are being assayed.

The aqueous solubilized protein composition formed after maintenance of the lysing reaction admixture usually contains cellular debris as well as solubilized protein. In preferred embodiments, the solubilized protein is separated from the cellular debris, typically by centrifugation.

To detect the presence of any solubilized surface immunocomplex formed, a portion of the aqueous solubilized protein composition is admixed with a solid support capable of specifically binding the immunocomplex, thereby forming a solid/liquid phase (capturing reaction) admixture.

Solid supports capable of specifically binding a solubilized surface immunocomplex are typically comprised of a specific binding agent affixed (operatively linked) to a solid matrix. Preferably, the solid phase-affixed specific binding agent is an antibody molecule capable of immunoreacting with the solubilized surface immunocomplex. It should be noted that an antibody capable of immunoreacting with either the antigen or the antibody of the surface immunocomplex can be used.

Useful solid matrices are well known in the art. Such materials are water insoluble and include the cross-linked dextran available under the trademark SEPHADEX from Pharmdcia, Piscataway, N.J.; agarose; polyvinylchloride, polystyrene, cross-linked polyacrylamide, nitrocellulose or nylon-based webs such as sheets, strips or paddles; or tubes, plates or the wells of a microtiter plate such as those made from polystyrene, polycarbonate or polyvinylchloride.

When present as part of a solid support, a specific binding agent is typically affixed to a solid matrix by adsorption from an aqueous medium, although other modes of affixation, such as covalent coupling, well known to those skilled in the art, can be used.

The solid/liquid phase admixture is maintained for a time period sufficient for any solubilized surface immunocomplex present to be bound by the solid support and thereby form a solid-phase bound complex. Preferably, the maintained solid support is then separated from any non-bound protein, typically by washing.

Assaying the maintained solid support for the presence of solid-phase bound complex thereby provides a means for detecting the presence of the surface antigen of interest in the cell sample. Such assaying is typically performed by forming a labeling reaction admixture by admixing the maintained solid support with a labeled specific binding agent capable of specifically binding the immunocomplex portion of the solid-phase complex. Preferably, the labeled specific binding is capable of binding either the antigen or the antibody of the surface immunocomplex when the surface immunocomplex is itself bound to the solid support.

The labeling reaction admixture is maintained for a time period sufficient for the labeled specific binding agent to react with (specifically bind) any solid-phase immunocomplex present and thereby form a labeled solid-phase product. Any non-bound labeled specific binding agent is then typically separated from the solid support.

The presence of any labeled solid-phase product formed is then determined by known assay procedures that depend, as is well known, on the type of label used. The presence of labeled solid-phase product indicates the presence of the surface antigen of interest in the cell sample.

As used herein, the terta "solubilized immunocomplex" means a complex formed of an antibody bound to a cell surface antigen epitope whose presence is sought that is formed by reacting the antibody and cell surface antigen epitope followed by lysis of the cell to form cellular debris and a solubilized immunocomplex. The immunocomplex can be present in the cell sample analyzed as obtained from a patient (donor) as where the cell sample is a platelet sample from a patient with immune thrombocytopenic purpura (ITP) that contains autoantibodies to a platelet antigen such as the glycoprotein IIb/IIIa complex or glycoprotein Ib. The immunocomplex can also be formed by immunoreaction of alloantibodies of a patient with platelets of other cells of a prospective donor. The immunocomplex can still further be formed by immunoreaction of antibodies to a major histocompatibility complex (MHC) antigen epitope such as an HLA class I or class II antigen epitope present on the surface of the cell.

Another assay method for detecting the presence of a cell surface antigen comprises the steps of providing an aliquot of cells to be assayed. The cells of such an aliquot that bear the surface antigen to be detected having an immunocomplex that contains an antibody to the antigen sought immunoreacted with the antigen. Here, again, the immunocomplex, if present, can be present in the sample as obtained from the patient (donor) or can be prepared after obtaining the cell sample. The cells of the aliquot are lysed to provide cellular debris, and when the immunocomplex was present in the aliquot, to form a solubilized immunocomplex. The presence of the solubilized immunocomplex is thereafter assayed for.

In preferred practice, the cellular debris formed in the lysis/solubilization step is separated from the solubilized immunocomplex by any convenient means such as centrifugation. The separated, solubilized immunocomplex is thereafter affixed to a solid phase support to form a solid phase-affixed immunocomplex. The affixation can be by physical adsorption, immunoreaction using solid phase-bound antibodies directed to the antibodies of the immunocomplex, like monoclonal mouse anti-human antibodies as are available from the American Type Culture Collection of Rockville, MD (ATCC) under the accession number HB43, or by binding with S. aureus protein A coated on the solid support. The immunocomplex is thereafter assayed for as a solid phase-affixed immunocomplex.

In one embodiment, the cells of the sample are platelets. In such an embodiment, the antibodies of the immunocomplex can be autoantibodies from the sample donor (patient) and those autoantibodies can be directed to the glycoprotein IIb/IIIa complex or glycoprotein Ib. In another embodiment, the platelets or other cells are from a first person (donor) and the antibodies of the immunocomplex can be alloantibodies from a second person (donee), as where cross-matching of platelets or other cells from a prospective donor, and serum or plasma from a patient (donee) provides the antibodies of the immunocomplex. The antibodies of the immunocomplex can also be directed to a group of cell surface antigens such as a tissue rejection-related antigen like an antigen of the MHC or an HLA antigen. Antibodies directed to an epitope present on substantially all HLA antigens as well as those directed to individual HLA-specific antigen epitopes are available from the ATCC as well as from the antiserum bank at the National Institutes of Health (NIH), Bethesda, Md.

Thus, a method is also provided for assaying platelet or other cellular compatibility between a donor and a patient (donee). In this method, an aliquot of serum or plasma from a patient suspected of having alloantibodies to a donor platelet or other cellular antigen is admixed with platelets or other cells of the donor to form an aqueous, liquid admixture. The admixture so formed is maintained under biological assay conditions for a predetermined time period sufficient for any alloantibodies present in the serum or plasma to immunoreact with the platelet or other cellular antigen to form an immunocomplex. The platelets or other cells of the admixture are lysed to form cellular debris and a solubilized immunocomplex, when the alloantibodies and platelet or other cellular antigen were present in the admixture. The presence of the immunocomplex is thereafter assayed for. If the immunocomplex is not found to be present, the donor and donee are compatible, and vice versa.

The present invention also provides a method for typing cells for the presence of various surface antigens such as HLA antigens. Here an aliquot of a cell sample to be typed is reacted with an antibody that reacts with an antigen epitope common to substantially all of the group of cell surface antigens to be assayed for such a monoclonal antibody that reacts with the backbone of the HLA antigen to form an immunocomplex. The cells are thereafter lysed to provide cellular debris and a solubilized immunocomplex. The solubilized immunocomplex is thereafter reacted with indicating paratopic molecules; i.e., whole antibodies or portions of antibodies that contain the paratope, that immunoreact with at least one member of the antigen group such as an HLA-specific antigen epitope to form a second immunocomplex. The presence of the second immunocomplex is then assayed for. Where HLA antigens are sought, the first-named antibodies and indicating paratopic molecules are available from the ATCC and the NIH.

Where a complete profile of cell surface antigens is desired, as where HLA typing is carried out, it is often convenient to divide the solubilized immunocomplex into a plurality of aliquots. The aliquots are thereafter individually reacted with members of a panel of indicating paratopic molecules, and the presence of second immunocomplex from each of panel members as assayed for.

The assay methods of the present invention utilize a solid support capable of specifically binding a solubilized immunocomplex. Useful solid supports are typically comprised of a specific binding agent affixed (operatively linked) to a solid matrix.

A specific binding agent can be linked to a label or indicating means and used to form a labeled immunoreaction product.

The terms "indicating means" and "label" are used herein to include single atoms and molecules that are capable of producing a detectable signal and of being linked to an antibody or used separately.

The indicating means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamin-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in Marchalonis et al., "Immunofluorescence Analysis" 189-231, supra, which is incorporated herein by reference.

In preferred embodiments, the indicating group is an enzyme, such as horseradish peroxidase (HRP), glucose oxidase, or the like. Where the principal indicating group is an enzyme such as HRP or glucose oxidase, additional reagents are required to visualize the fact that a complex (immunoreaction product) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein.

An exemplary radiolabeling agent is a radioactive element that produces gamma ray emissions. Elements which themselves emit gamma rays, such as $^{124}I$, $^{125}I$, $^{128}I$, $^{131}I$, $^{132}I$ and $^{51}Cr$ represent one class of gamma ray emission-producing radioactive element indicating groups. Particularly preferred is $^{125}I$. Another group of useful indicating groups are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium.

The labeling of proteinaceous specific binding agents is well known in the art. For instance, antibodies produced by hybridomas can be labeled by metabolic incorporation of isotope containing amino acids provided as a component in the tissue culture medium. See for example Galfre et al., *Meth. Enzymol.*, 73:3-46 (1981). The techniques of protein conjugation or coupling through activated functional groups are particularly applicable. See, for example, Aurameas, et al., *Scand. J. Immunol.*, Vol. 8, Suppl. 7:7-23 (1978) and U.S. Pat. No. 4,493,795 which is incorporated herein by reference. Methods for conjugating enzymes to proteins may be found in U.S. Pat. No. 3,791,932 and U.S. Pat. No. 3,839,153. In addition, site directed coupling reaction can be carried out so that the label does not substantially interfere with the immunoreaction of the second receptor with apo B-100. See, for example, Rodwell et al., *Biotech.*, 3:889-894 (1985).

EXAMPLES

The following examples are intended to illustrate, but not limit, the present invention.

1. Characterization of the Antiplatelet Immune Status of Autoimmune Individuals

A. Study Subjects

I studied plasma or platelet samples obtained between Jan. 1, 1982 and Jul. 1, 1986 from 44 patients with chronic ITP, 20 control subjects and 20 thrombocytopenic controls (acute non-lymphocytic leukemia, 3 patients; acute lymphoblastic leukemia, 2 patients; bone marrow transplantation patients with anti-HLA antibodies, 3 patients; aplastic anemia, 2 patients; non-Hodgkins lymphoma, 3 patients (one with cryoglobulins); cirrhosis, one patient; myeloproliferative disease, 3 patients; and carcinoma on chemotherapy, 3 patients). Patients with ITP were thrombocytopenic with normal or increased numbers of megakaryocytes and without evidence of other types of immune thrombocytopenia.

B. Assays for Antiglycoprotein Autoantibody

The specificity of both the immunobead and microtiter assays is determined by the monoclonal antiglycoprotein antibody employed. The following murine monoclonal antibodies were used: anti-GPIIb/IIIa-2A9, 3F5, 2G12 (provided by Dr. V. L. Woods) - 2A9 is specific for GPIIb and the others are complex-specific; anti-GPIb-P3 (provided by Drs. Zaverio Ruggeri and Theodore Zimmerman, Scripps Clinic); and antihuman IgG (American Type Culture Collection, Rockville, Md., ATCC HB-43). Monoclonal antibodies (50 ug) were labeled with 500 uCi of $^{125}I$ using the chloramine-T method. All incubations in both assays were carried out at room temperature.

It is known that in detergent extracts GPIIb and GPIIIa form a complex and that GPIb is complexed with platelet glycoproteins IX and V. Therefore, as measured by these two assays, anti-GPIIb/IIIa autoantibodies could be against epitopes on either GPIIb or GPIIIa and anti-GPIb specific for GPIb, GP V or GP IX. However, for the purposes of this report, results will be reported as either anti-GPIIb/IIIa or anti-GPIb referring to autoantibodies against proteins of the GPIIb/IIIa complex or the GPIb complex.

C. Immunobead Assay

This assay can be used to measure either platelet-associated autoantibody or plasma autoantibody.

(i) Immunobead Preparation

Anti-IgG-coated immunobeads were prepared by incubating polystyrene beads (Poly-Sep, Polysciences Inc., Warrington, Pa.) with murine monoclonal antihuman IgG (ATCC HB-43) in saline for 60 min at a bead-/antibody ratio of 2000:1 by weight (e.g., 100 mg of beads to 50 ug of anti-IgG in 2 ml of saline). The beads were then centrifuged for 10 sec at maximum speed in a tabletop centrifuge (International Clinical Centrifuge, Model 65133M). After washing once with 10 ml of 0.05% Tween-20 in phosphate-buffered saline, pH 7.4 (PBS-Tween), nonspecific binding sites are blocked by incubation of the beads in 2% bovine serum albumin (BSA) in PBS-Tween for 60 min followed by four washes in PBS-Tween.

(ii) Platelet Preparation

Platelets from EDTA-anticoagulated blood were obtained from the patient or from a normal donor and washed six times with 0.05M isotonic citrate buffer. To prepare antibody-sensitized platelets, washed normal platelets ($10^8$ in 0.1 ml) were incubated with 1.0 ml of patient or control plasma, containing $PGE_1$ (1 ug/ml) and theophylline (1 uM), for 60 min at room temperature and then washed four times with 0.05 M citrate buffer containing $PGE_1$ and theophylline. Patient platelets ($10^8$) or the antibody-sensitized platelets were resuspended in 900 ul of citrate buffer containing leupeptin (100 ug/ml) and then solubilized by adding 100 ul of 10% Triton X-100. Control samples were handled similarly.

(iii) Assay

The solubilized platelets from each sample were centrifuged at 12,000 xg for 5 min. Preliminary studies showed that this step was required, particularly in anti-GPIb autoantibody studies, to prevent falsely elevated values. The supernate is then incubated for 60 min with 100 mg of anti-IgG-coated immunobeads to allow attachment of IgG and any bound antigen. After four washes with PBS-Tween, the presence of specific antigen is demonstrated by incubating the beads with 1.0 ml of PBS-Tween containing about 400,000 cpm of $^{125}$I monoclonal antibody specific for either anti-GPIIb/IIIa (a cocktail of 3 monoclonal antibodies specific for non-competing sites, 2A9, 3F5, and 2G12) or anti-GPIb (P3) for 60 min at room temperature and then washing four times with PBS-Tween. The beads were resuspended in 1 ml of buffer and 0.5 ml was removed for determining radioactivity. Data are expressed as a binding ratio of cpm of patient sample/mean cpm of three control samples. The mean percent variation results of replicate samples of control platelets and platelets sensitized with control plasma were: anti-GPIIb/IIIa-10.1±7.5 (14 studies) and 9.1±8.1 (31 studies), respectively, and anti-GPIb- 6.8±7.0 (17 studies) and 7.9±7.6 (24 studies), respectively. Patient samples with a binding ratio of >1.3 are considered positive (>2 S. D. over control). Preliminary studies show that positive reactivity can be removed by adsorption of plasma with excess platelets. In addition, storage of samples for up to four days at 4° C. did not affect platelet or plasma control values.

D. Microtiter Well Assay

Details have been previously published (Woods et al., *Blood*, 63:368–375 (1984) and Woods et al., *Blood*, 64:156–160 (1984)). Briefly, washed platelets ($10^9$ ml) or CEM leukemic cells ($10^7$ ml) in PBS containing leupeptin (100 ug/ml) were solubilized in 1% Triton X-100 for 30 min at 4° C. and then ultracentrifuged (100,000 xg for 60 min). The lysates are stored at −70° C. Microtiter wells are coated overnight at 5° C. with 100 ul of either anti-GPIIb/IIIa (2A9 or 3F5) or anti-GPIb (P3) at a concentration of 5 ug/ml. After six washes with 200 ul of PBS-Tween, the remaining binding sites were blocked for 50 min with 200 ul of 2% BSA in PBS-Tween. After six washes with PBS-Tween, 100 ul of platelet lysate or the antigen negative CEM lysate, diluted 1:10, were added and incubated for 50 min. This allows attachment of the specific platelet antigen to the well-bound monoclonal antibody. After six washes, appropriate dilutions (1:10 for screening plasma and higher dilutions if positive) of patient or control plasma were added and incubated for 50 min. After six washes, 100 ul of radiolabeled murine monoclonal antihuman IgG (about 100,000 cpm) were added and after 50 min incubation and six final washes, the radioactivity of each well was determined. The percent variation for replicate control plasmas is −5.0±7.7 for anti-GPIIb-/IIIa and −1.9±6.4 for anti-GPIb (Woods et al., *Blood*, 63:368–375 (1984) and Woods et al., *Blood*, 64:156–160 (1984)). Samples with a percent increase of >11 were considered positive (>2 S. D.).

E. Results (i) Chronic ITP Patients

The results were divided into two groups for evaluation: (1) pre-splenectomy patients—the initial study sample was obtained prior to splenectomy although in some of these patients additional studies were also performed after surgery; (2) posts-plenectomy patients—the patient was first studied after surgery.

(ii) Pre-Splenectomy Studies (Table 1)

Twenty-six patients were studied; 16 subsequently had their spleens removed and eight entered a complete remission, six were splenectomy failures and two were lost to follow up. Platelet-associated autoantibody was measured using the immunobead assay in seven of the 26 patients. Of these, six (85.7%) were positive with ratios ranging from 4.9 to 30.1 (control valued <1.3); five had anti-GPIIb/IIIa and one had anti-GPIb autoantibodies.

TABLE I

| | | | | | | | | | | |
|---|---|---|---|---|---|---|---|---|---|---|
| ANTI-PLATELET GLYCOPROTEIN AUTOANTIBODIES PRE-SPLENECTOMY CHRONIC ITP PATIENTS | | | | | | | | | | |
| Patient Number | Platelet Count (per mm³) | Splx | Resp | PAIgG | Anti-GPIIb/IIIa | | | Anti-GPIb | | |
| | | | | | Immunobead | | | Immunobead | | |
| | | | | | P-Assoc | Plasma | Well | P-Assoc | Plasma | Well |
| 1 | 2000 | Yes | ? | — | 16.7 | 2.3 | Neg | — | 0.8 | Neg |
| 2 | 9000 | Yes | CR | — | — | 0.8 | Neg | — | 1.0 | Neg |
| 3 | 9000 | Yes | CR | — | — | 0.9 | Neg | — | 0.9 | Neg |
| 4 | 9000 | Yes | NR | — | — | 4.5 | Neg | — | 0.9 | Neg |
| 5 | 10000 | No | — | — | — | 0.9 | Pos(320) | — | 1.0 | Pos(80) |
| 6 | 14000 | Yes | NR | — | — | 1.5 | Neg | — | 1.1 | Neg |
| 7 | 18000 | Yes | CR | 12962 | — | 0.6 | Neg | — | 1.0 | Neg |
| 8 | 19000 | No | — | 4423 | — | 1.4 | Neg | — | 0.9 | Neg |
| 9 | 20000 | No | — | 4873 | — | 1.3 | Neg | — | 0.9 | Neg |
| 10 | 23000 | Yes | CR | — | — | 1.7 | Neg | — | — | Neg |
| 11 | 34000 | Yes | CR | 7353 | — | 1.6 | Neg | — | — | Neg |
| 12 | 39000 | No | — | 30990 | — | 0.9 | Neg | — | 2.0 | Neg |
| 13 | 40000 | Yes | NR | 3453 | — | 1.0 | Neg | — | 0.9 | Neg |
| 14 | 40000 | Yes | NR | — | 30.1 | 5.5 | Neg | — | 1.1 | Neg |
| 15 | 42000 | No | — | — | 0.6 | 0.7 | Neg | 1.0 | 1.2 | Neg |
| 16 | 46000 | No | — | 9036 | — | 1.1 | Neg | — | 0.8 | Neg |
| 17 | 50000 | Yes | NR | 11049 | — | 0.9 | Neg | — | 0.9 | Neg |
| 18 | 50000 | Yes | NR | 17143 | 16.1 | 3.9 | Neg | — | 0.8 | Neg |
| 19 | 50000 | No | — | — | 10.0 | 2.5 | Neg | — | 0.8 | Neg |
| 20 | 69000 | No | — | 7286 | 0.7 | 0.6 | Neg | 4.9 | 1.8 | Neg |
| 21 | 85000 | Yes | CR | 1351 | — | 1.2 | Pos(640) | — | — | Neg |
| 22 | 100000 | No | — | — | — | 0.9 | Neg | — | 1.2 | Neg |
| 23 | 106000 | Yes | CR | 5152 | 16.2 | 1.4 | Neg | — | — | Neg |
| 24 | 112000 | No | — | 3537 | — | 0.9 | Neg | — | 3.6 | Pos(40) |
| 25 | 145000 | Yes | ? | 3692 | — | 3.1 | Neg | — | 1.1 | Neg |

TABLE I-continued
ANTI-PLATELET GLYCOPROTEIN AUTOANTIBODIES
PRE-SPLENECTOMY CHRONIC ITP PATIENTS

| Patient Number | Platelet Count (per mm³) | Splx | Resp | PAIgG | Anti-GPIIb/IIIa Immunobead P-Assoc | Anti-GPIIb/IIIa Plasma | Anti-GPIIb/IIIa Well | Anti-GPIb Immunobead P-Assoc | Anti-GPIb Plasma | Anti-GPIb Well |
|---|---|---|---|---|---|---|---|---|---|---|
| 26 | 26100 | Yes | CR | 3075 | — | 0.8 | Neg | — | 1.2 | Neg |

Splx - splenecotomy:
Resp - response;
CR - Normalization of platelet count;
NR - no response or relapse after an initial response or ? if lost to follow-up;
PAIgG - platelet-associated IgG (ng/$10^9$ plts);
Immunobead - results of platelet-associated (P-Assoc) or plasma immunobead assay expressed as a ratio of patient/control results (positive > 1.3);
well - results of microtiter well assay expressed as negative (Neg) or positive (Pos) with titers of positive tests shown in parenthesis.

Platelet-associated autoantibodies in three of these patients (patients 14, 18 and 23) were also studied after splenectomy (Table 2). In the patient who attained a complete remission (patient 23), the anti-GPIIb/IIIa autoantibodies present prior to splenectomy were no longer demonstrable after surgery. In the two others, the autoantibodies persisted despite splenectomy and although both obtained a temporary increase in the platelet count after surgery (135,000/mm³ in one and 313,000/mm³ in the other), they both became severely thrombocytopenic (<20,000) within a few weeks after surgery. Table 2 also compares the platelet-associated IgG (PAIgG) and the platelet-associated anti-GPIIb/IIIa values prior to and after splenectomy. In patient 23, who attained a complete remission, and patient 14, who responded only partially, the values of both determinations varied concordantly. However, in patient 18 whose platelet count became normal briefly after surgery but who later relapsed (platelet count 14,000/mm³), the PAIgG values became normal in concert with the platelet count but the platelet-associated anti-GPIIb/IIIa remained elevated.

Plasma autoantibodies were studies in all patients using both assays; 16/26 (61.5%) were positive in at least one of the assays. Eleven had circulating anti-GPIIb/IIIa and three had anti-GPIb autoantibodies when studied using the immunobead assay; ratios varied from 1.4 to 5.5. Of these patients with positive immunobead assays, only one (patient 24) was also positive using the microtiter assay. Two patients with negative immunobead assays (patients 5 and 21) were positive using the microtiter assay; one of these (patient 5) had antibody in the microtiter assay to both GPIIb/IIIa and GPIb.

TABLE 2
THE EFFECT OF SPLENECTOMY ON ANTI-GPIIb/IIIa
AUTOANTIBODY AND PLATELET-ASSOCIATED IgG

| Patient | Sample* Day | Therapy | Platelet Count (per mm³) | Anti-GPIIb/IIIa (Ratio) | PAIgG (ng per $10^9$ plts) |
|---|---|---|---|---|---|
| 14 | −25 | P | 40,000 | 28.8 | 8,900 |
|  | 0 | P | 96,000 | 21.2 | 5,847 |
|  | +5 | — | 135,000 | 25.4 | 6,595 |
|  | +52 | — | 109,000 | 31.1 | 19,500 |
| 18 | −111 | — | 51,000 | — | 17,140 |
|  | 0 | P | 118,000 | 16.1 | 4,400 |
|  | +5 | — | 103.000 | 13.7 | 4,394 |
|  | +8 | — | 313,000 | 11.3 | 2,611 |
| 23 | −1 | P | 106,000 | 16.2 | 5,152 |
|  | +28 | — | 465,000 | 1.0 | 985 |
| Control Values |  |  | 180–400,000 | <1.3 | <3,300 |

Anti-GPIIb/IIIa - platelet-associated autoantibodies against the platelet glycoprotein IIb/IIIa complex measured by the immunobead assay;
PAIgG - platelet-associated IgG;
P - high dose prednisone;
*Number of days before (−) or after splenectomy; day 0 is the day of surgery.

(iii) Post-Splenectomy Studies (Table 3)

All patients in this group failed to maintain a normal platelet count after splenectomy. Platelet-associated autoantibody was measured using the inunnobead assay in four of the 18 patients in this group. Three were positive, one with autoantibodies against GPIIb/IIIa and the other two against GPIb.

Plasma autoantibodies were demonstrable using the immunobead assay in ten of the 18 patients (55%), seven with anti-GPIIb/IIIa and three with anti-GPIb. Seven of the ten patients with positive immunobead assays also had autoantibodies of the same specificity shown by the microtiter assay. Two patients (patients 9 and 12) were positive in the microtiter assay but negative by the immunobead method. One patient (patient 4) had autoantibodies against both antigens.

(iv) Thrombocytopenic Controls

Platelets (eight patients) and plasma (20 patients) from patients with non-immune thrombocytopenia were studied using both assays. Negative results were obtained in every instance using both the immunobead and the microtiter assays (data not shown).

TABLE 3
ANTI-PLATELET GLYCOPROTEIN AUTOANTIBODIES
POST-SPLENECTOMMY CHRONIC ITP PATIENTS

| Patient | Platelet Count (per mm³) | PAIgG | Anti-GPIIb/IIIa Immunobead P-Assoc | Anti-GPIIb/IIIa Plasma | Anti-GPIIb/IIIa Well | Anti-GPIb Immunobead P-Assoc | Anti-GPIb Plasma | Anti-GPIb Well |
|---|---|---|---|---|---|---|---|---|
| 27 | 1000 | — | — | — | Neg | — | 3.3* | Pos(6400) |
| 28 | 3000 | — | — | 2.2 | Neg | — | ( ) | Neg |
| 29 | 3000 | 6911 | — | 1.0 | Neg | — | 1.0 | Neg |
| 30 | 3000 | 59800 | — | 1.3 | Pos(40) | — | 2.6 | Pos(80) |
| 31 | 6000 | — | 7.0** | 9.4 | Pos(640) | — | 1.2 | Neg |

TABLE 3-continued
ANTI-PLATELET GLYCOPROTEIN AUTOANTIBODIES
POST-SPLENECTOMMY CHRONIC ITP PATIENTS

| Patient | Platelet Count (per mm$^3$) | PAIgG | Anti-GPIIb/IIIa Immunobead P-Assoc | Anti-GPIIb/IIIa Immunobead Plasma | Anti-GPIIb/IIIa Well | Anti-GPIb Immunobead P-Assoc | Anti-GPIb Immunobead Plasma | Anti-GPIb Well |
|---|---|---|---|---|---|---|---|---|
| 32 | 6000 | — | — | 0.9 | Neg | - | 0.9 | Neg |
| 33 | 7000 | 53000 | — | 5.2 | Pos(320) | — | 0.9 | Neg |
| 34 | 7000 | — | — | 1.2 | Neg | 17.2 | 2.0 | Pos(20) |
| 35 | 9000 | — | — | 0.6 | Neg | 1.0 | 0.9 | Pos(40) |
| 36 | 9000 | — | — | 1.0 | Neg | — | 1.1 | Neg |
| 37 | 13000 | — | — | 2.5 | Neg | — | 0.9 | Neg |
| 38 | 14000 | — | 0.6 | 0.7 | Neg | 5.7 | 1.3 | Pos(80) |
| 39 | 21000 | 42396 | — | 3.8 | Neg | — | 0.8 | Neg |
| 40 | 24000 | 6326 | — | 0.9 | Neg | — | 1.1 | Neg |
| 41 | 34000 | — | — | 0.6 | Neg | — | 1.0 | Neg |
| 42 | 40000 | 5650 | — | 2.6 | Neg | — | 1.1 | Neg |
| 43 | 42000 | 19024 | — | 1.0 | Neg | — | 0.9 | Neg |
| 44 | 117000 | 11795 | — | 2.1 | Pos(40) | — | 1.1 | Neg |

PAIgG - platelet-associated IgG (ng/10$^9$ plts);
immunobead - results of platelet-associated (P-Assoc) or plasma immunobead assay expressed as a ration of patient-/control results (positive > 1.3);
well - results of the microtiter well assay expressed as negative (neg) or positive (pos) with titers of positive tests shown in parenthesis.
*0.1 ml of plasma used to sensitize platelets.
**0.18 × 10$^8$ platelets assayed.

F. Discussion

The above results illustrate experience with two methods for measuring antiplatelet autoantibodies in chronic ITP: the immunobead assay which is capable of measuring both platelet-associated and plasma autoantibodies and the microtiter assay useful in detecting only plasma antibodies.

Platelet-associated autoantibodies were noted in nine of 11 ITP patients (81.8%; seven with anti-GPIIb/IIIa and two with anti-GPIb). Although the number of patients studied is too small to evaluate statistically, positive tests were seen in about the same frequency in thrombocytopenic patients studied first pre-or post-spenectomy.

Plasma autoantibodies were noted in a lesser frequency; 28/44 were positive (63.6%). Using the immunobead assay, 24/44 patients had demonstrable circulating autoantibody (18 with anti-GPIIb/IIIa and six with anti-BPIb). Fewer positive samples were noted using the microtiter assay as reported previously (Woods et al., Blood, 63:368–375 (1984) and Woods et al., Blood, 64:156–160 (1984)). Only 12/44 patients were positive using this assay (five with anti-GPIIb/IIIa, five with anti-GPIb and two with both). Three patients had autoantibodies demonstrable only with this method. This assay was positive in almost one-half of the post-spenectomy patient group (all who were refractory) while only three of the 26 patients in the pre-operative group were positive. Whether this assay predicts more severe disease or reflects the tendency of our laboratory to receive samples from more severely affected patients is not known.

These autoantibody assays have distinct advantages over assays for platelet-associated IgG (PAIgG). First, they allow the direct demonstration of either platelet-associated or plasma autoantibodies against defined platelet proteins confirming the autoimmune nature of the patient's disease. Conversely, the PAIgG assay measures IgG on platelets of unknown specificity. The adaptation of the PAIgG assay used by van Leeuwen et al., Blood, 59:23–26 (1982), where the relative binding to normal and thrombasthenic platelets is used can provide similar although indirect information in patients with anti-GPIIb/IIia antibodies but the method is cumbersome and thrombasthenic platelets are not available to more laboratories. It is of interest that my rate of anti-GPIIb/IIIa positivity, using the combination of assays, is quite similar to theirs. Second, autoantibody test results in patients with non-immune thrombocytopenia have thus far been completely negative with these two assays while PAIgG results are positive in many patients with a variety of diagnoses (Mueller-Eckhardt et al., Br. J. Haematol., 52:49–58 (1982) and Kelton et al., Blood, 60:1050–1053 (1982)). Although it seems likely, as suggested by the studies of Kelton et al. (supra), that positive PAIgG results may reflect immune-mediated platelet destruction, it must be acknowledged that an increase in PAIgG does not necessarily show the presence of autoantibody. A divergence between anti-GPIIb/IIIa and PAIgG results noted in one of our ITP patients (patient 18) supports this contention. Her autoantibody values remained elevated after splenectomy despite normalization of both the platelet count and the PAIgG results. This patient subsequently relapsed, suggesting that this assay may be useful in predicting the ultimate outcome of splenectomy. Obviously these data are preliminary. Although autoantibodies were not seen in the group of thrombocytopenic control patients reported here, it seems likely that when patients with collagen vascular disease or lymphoma are screened using these assays that positive results maybe seen in some of these patient groups since they have been shown to have other types of autoantibodies (e.g., anti-RBC antibodies).

The difference in the results between the immunobead and microtiter well assays is of interest. It is known from the study of purified protein antigens that there are two types of epitopes: sequential and topographic (Berzofsky, Science, 229:932–940 (1985)). Seqpaential epitopes involve amino acid sequences of one section of the protein while topographic epitopes involve regions of the molecule remote in sequence but close in three dimensional space due to the tertiary molecular structure. The most likely explanation for the greater percent positivity with the inununobead assay is that solubilization of the platelets prior to incubation with antibody, which is required for the microtiter assay, in some way disturbs the antigenic epitope while incubation of antibody and platelets prior to solubilization stabilizes it. I postulate that the microtiter assay measures sequential or stable topographic epitopes while the immunobead assay measures unstable topographic epitopes as well. Preliminary studies in my laboratory comparing the ability of plasma autoantibodies to precipitate the GPIIb/IIIa complex after incubation of plasma with surface-labeled platelets to that of precipitating radiolabeled purified GPIIb/IIIa support this hypothesis. Plasmas positive in both the microtiter and immunobead assays (three studied) are capable of precipitating both the purified GPIIb/IIIa complex and the complex from surface-labeled platelets while plasmas positive in the immunobead but negative in the microtiter assay (four studied) are able to precipitate only the complex from surface-labeled platelets. Obviously, further studies will be needed to confirm these preliminary findings.

These assays are both adaptable to the measurement of another as yet-unidentified autoantibodies when appropriate monoclonal antibodies become available. Since many patients with chronic ITP have no demonstrable autoantibody, it seems likely that autoantibodies against other platelet-associated antigens (e.g., phospholipids, glycolipids, etc.) are present.

In summary, the present studies describe the use of two assays for the measurement of autoantibodies to specific platelet proteins. Results show that the majority of patients with chronic ITP have autoantibodies against either the platelet GPIIb/IIIa complex or against GPIb. Differences in the frequency of positive results seen in the two assays provide evidence for epitopes which have varying degrees of stability upon solubilization.

2. Antiplatelet Immune Status Characterization in Platelet Transfusion Patients

A. Patient and Donor Population

Fifty one transfusion episodes involving 7 patients with bone marrow failure were studied (Table 4). All were refractory to random donor platelets prior to entry on study. Transfusion episodes associated with fever, infection or spenomegaly were not routinely excluded if good increments from any donor were seen within 24 hours. No patient demonstrated evidence of DIC during the study period. Patient 1 was dropped from the study when he became refractory to all donors a few days before his death, associated with ARDS and mechanical ventilation. Patient 2 was dropped from the study when he became persistently febrile and refractory to all donors. He was subsequently determined to have a disseminated fungal infection. Donors were selected from family members when possible (n-16), otherwise from paid community volunteers (n-35). HLA matching was as follows: A-9; B,B2X-5; C-19; D-8; unknown, related-7, unknown, unrelated-3.

TABLE 4
PATIENT CHARACTERISTICS

| Patient | Age/Sex | Diagnosis | Evaluable Transfusions | Number of Different Donors |
|---|---|---|---|---|
| 1 | 42/M | AA, allo-BMT | 22 | 14 |
| 2 | 32/M | ALL, auto-BMT | 2 | 2 |
| 3 | 21/M | AML | 5 | 3 |
| 4 | 36/F | AML | 2 | 2 |
| 5 | 41/M | AML | 1 | 1 |
| 6 | 71/M | AML | 17 | 11 |
| 7 | 57/M | 2°MDS->AML | 2 | 2 |
| | | Totals | 51 | 35 |

TABLE 4-continued

AA - aplastic anemia;
allo-BMT - allogenic bone marrow transplantation;
auto-BMT - autologous bone marrow transplantation;
AML - acute myelogenous leukemia;
MDS - myelodysplastic syndrome.

B. Assessment of Transfusion Outcome

Each transfusion episode was evaluated by computing the 1 hour corrected count increment (CCI) from the following standard formula:

$$\frac{1 \text{ hr. post} - \text{pre-transfusion count} \times BSA}{\text{number of platelets transfused}/10^{11}} = 1 \text{ hour } CCI$$

$BSA$ = body surface area in $M^2$

When available, a later CCI (8 to 24 hours) was also calculated. A successful outcome was defined as a 1 hour CCI of >7500. In one instance, a 1 hour CCI of 7289 with a 6 hour CCI of 4252 was considered "successful" when a transfusion from an HLA matched sibling given less than 24 hours later gave a 1 hour CCI of 8391 and 6 hour CCI of 2670. In 2 instances where 1 hour post platelet counts were not available, an 8 hour CCI <0 not associated with overt nonimmunologic causes of poor platelet survival was considered as evidence of an unsuccessful transfusion outcome.

C. Murine Monoclonal Antibodies

HB-43 is an IgG kappa antibody derived from the 1410K67 cell line, which recognizes the Fc portion of human IgG. HB-95 is an $IgG_2$ antibody derived from the W6/32 cell line, which recognizes a monomorphic epitope on the heavy chain of human HLA A, B and C antigens. The intact heterodimer is required for full expression of the epitope, although HB-95 binds weakly to isolated heavy chains. Both cell lines were obtained from the American Type Culture Collection (Rockville, Md.) and were used to produce ascites in Pristane-primed BALB/c mice, from which antibody was purified by protein A affinity chromatography.

$^{125}I$ labeling was accomplished by the chloramine-T procedure.

D. Preparation and Storage of Platelets (i) Normal Platelets

Blood from normal adult volunteers was drawn into EDTA and platelet-rich plasma separated by centrifugation at 400 g for 10 minutes. The platelets were pelleted by centrifugation at 1000 g for 15 minutes, washed 4 times with 1.0 ml of 0.05 M citrate buffer (14.7 g sodium citrate, 5.9 g sodium chloride, 25.0 g dextrose in 1,000 ml distilled $H_2O$; adjusted to pH 6.2 with 0.05 M citric acid), and resuspended in citrate buffer to approximately $10^9$/ml. Platelets were used fresh or stored in suspension at 4° C. for 24-48 hours.

(ii) Donor Platelets

Approximately 3 ml of platelet concentrate was obtained at the end of each phoresis procedure. This was divided into 1 ml aliquots and centrifuged at 750 g for 90 seconds to remove red cells. The platelets were centrifuged at 3000 g for 5 minutes and washed 4 times. The platelet concentrate could be kept for 24–48 hours at 4° C. prior to washing without affecting assay results.

(iii) Platelet Storage

To assess the effect of storage on the immunobead assay, 1.0 ml platelet aliquots ($1.3 \times 10^9$) from 2 normal donors were stored both in suspension at 4° C. and by freezing in liquid nitrogen, then tested at intervals of 1, 6, 15, 30 and 60 days against 2 control plasmas and 2 plasmas known to contain high titer anti-HLA antibodies. Platelets to be frozen were suspended in autologous plasma with 5% dimethylsulfoxide in plastic tubes, frozen at −70° C. overnight and then kept in liquid nitrogen. After thawing in a 37° C. waterbath, they were washed twice, resuspended in approximately 1 ml of citrate buffer and counted. Parallel aliquots were suspended in normal saline with 0.02% sodium azide in plastic tubes and kept at 4° C. Prior to assay, the platelets were resuspended by pipetting, washed twice and counted.

E. Preparation and Storage of Plasma and Serum

All assays were conducted using plasma, except as noted. Plasma was separated from EDTA anticoagulated whole blood by centrifugation at 1000 g for 15 minutes and kept in polypropylene tubes. Test plasma was obtained from recipients prior to transfusion and after any preceding transfusions whenever possible. In no case was test plasma obtained after the transfusion of interest. Positive control plasmas were obtained from multiply transfused individuals with known high-titer broad spectrum anti-HLA antibodies, as demonstrated with the immunobead assay against a panel of normal platelets. Negative control plasmas were obtained from normal volunteers with no history of transfusion or pregnancy. Both positive and negative control plasmas were ultracentrifuged at 100,000 rpm for 1 hour. All plasmas were used fresh or stored frozen at −70° C. Repeated freezing and thawing was avoided.

Sera were prepared from a small number of positive and negative control plasmas by incubation in glass tubes in the presence of CaCl and thrombin. Complement was inactivated with 0.02 M EDTA.

F. The HLA Immunobead Assay

Aliquots of $10^8$ donor platelets were sensitized by incubation with 100 ul of test or control plasma for 1 hour in plastic tubes. The sensitized platelets were washed three times, resuspended in 900 ul of citrate buffer, and solubilized by adding 100 ul of 10% Triton X-100. If the assay was to be completed the same day, the lysate was centrifuged at 3000 g for 5 minutes and the supernatant transferred to 15 ml polypropylene tubes. The lysate could be frozen at −20° C. following solubilization and the assay completed at a later date without affecting results.

Immunobeads were prepared by incubating ¼ inch polystyrene beads (#0023804, Pierce Chemical Co., Rockford, Ill.) with anti-human IgG (HB-43, 10 ug per bead) in 500 ul per bead of 0.01 M $NaHCO_3$ buffer (pH 8.5) for 1 hour on a rotator. After 4 washes with 1.0 ml PBS-Tween they were incubated for an additional hour with 2% bovine serum albumin (1 ml per bead) to block residual binding sites. Following 4 more washes, 1 bead was added to each tube containing platelet lysate and incubated with constant agitation for 1 hour. During this incubation, IgG alloantibodies which had been bound to the platelet before solubilization attach via the Fc portion to the HB-43 bound to the bead. The class I HLA antigen remains bound to the Fab portion of the alloantibody after solubilization, and is thus bound indirectly to the bead. The beads were washed 4 more times in PBS-Tween, and incubated for 1 hour with 400,000 cpm of $^{125}$I-labeled monoclonal anti-HLA antibody (HB-95) in 1 ml PBS-Tween. Following 4 final washes, the beads were dried on a paper towel and counted in a Beckman gamma counter. All incubations were carried out at room temperature.

The assay of interest was run in triplicate along with duplicates of 1 positive and 2 negative controls. One technician could run 24 simultaneous assays in approximately 6 hours.

G. Radioactive Antiglobulin Test (RAGT)

The RAGT was performed by a modification of the method of LoBuglio et al.[27] Briefly, $10^8$ washed platelets were sensitized by incubation with 100 ul of plasma for 1 hour at room temperature, then washed three times in citrate buffer. A $3 \times 10^7$ aliquot was incubated for 30 minutes with 300,000 cpm of $^{125}$I-labeled anti-human IgG (HB-43). Triplicate 50 ul aliquots containing $6 \times 10^6$ platelets were layered over 200 ul of 30% sucrose in 400 ul plastic microcentrifuge tubes with tapered tips and centrifuged at 11,000 g for 5 minutes. After quick-freezing at −70° C., the tips containing the platelet button were removed and counted in a Beck/nan gamma counter.

H. Transfusion Study Results (i) Characterization of the HLA Immunobead Assay

Triplicate assays using 12 negative control plasmas against the same normal platelets gave a mean percent variation of 8.7+/−9.0 (1 SD). Absolute values of negative controls generally fell in the range of 80–300 cpm. A single negative control plasma was also tested against the same platelets 10 times, giving a mean per cent variation of 6.3+/−6.6%. Assays run using citrate buffer in place of plasma gave results comparable to negative controls.

To assess the possibility that the assay might recognize antiplatelet antibodies directed against non-HLA antigens, plasmas from 18 patients with the clinical syndrome of ITP were tested against normal platelets. Seven of these had plasma autoantibodies to the glycoprotein IIb/IIIa complex, 2 had autoantibodies to glycoprotein Ib, and the remainder gave negative results for both these autoantibodies. Three plasmas gave positive results in the immunobead assay, 2 with GP IIb/IIIa autoantibodies and one with a strong antiplatelet autoantibody without demonstrable specificity. All 3 patients had a history of pregnancy and/or transfusion, suggesting coexisting alloantibodies.

Seven positive and 7 negative controls were run using serum and compared to results using plasma. No significant difference was noted between negative controls. The absolute value of serum positive controls averaged 60% of plasma values. No positives were missed by using serum.

(ii) Interpretation of Assay Results

The mean test result was divided by the mean of the negative controls to give a test/control ratio (TCR). Experiments with 12 normals gave a mean normal TCR of 1.00+/−0.14 (1 SD). A TCR of <1.43 was initially defined as negative, to include 3 standard deviations. In practice, TCRs between 1.43 and 3.0 were associated with successful transfusion outcomes in 5 of 6 cases (Table 5). This was interpreted as evidence that the immunobead assay can detect levels of alloantibody below that necessary to significantly affect platelet survival. That this was not due to random variation is supported by the observation that all 9 A match transfusions were associated with TCRs <1.43. For clinical purposes, therefore, a TCR of </=3.0 was considered "negative" and predictive of a successful transfusion outcome.

A TCR of </=2.0 was empirically defined as negative for the RAGT by similar retrospective data analysis.

TABLE 5

TRANSFUSION EPISODES WITH TCRs BETWEEN 1.43 AND 3.00

| Patient | Mean Test CPM | Mean Control CPM | TCR | 1 Hour CCI |
|---|---|---|---|---|
| 1 | 344 | 197 | 1.75 | 2659 |
| 2 | 390 | 150 | 2.61 | 17396 |
| 3 | 123 | 81 | 1.53 | 11481 |
| 4 | 380 | 166 | 2.29 | 10298 |
| 5 | 505 | 169 | 2.99 | 12269 |
| 6 | 266 | 143 | 1.86 | 11538 |

TCR - test/control ratio;
CPM - gamma counts per minute (iii) Correlation With Transfusion Outcome Each valuable transfusion episode was categorized according to whether the immunobead assay was positive (TCR>3.0) or negative (TCR</=3.0), and the outcome successful (1 hour CCI >/=7500) or unsuccessful (1 hour CCI <7500). The data for both the immunobead assay and the RAGT are summarized in Table 6. The immunobead assay was positive in 18 episodes; 16/18 (88.9%) had unsuccessful outcomes. In 33 cases the assay was negative; 29/33 (87.9%) had successful outcomes. The mean 1 hour CCI was 2199 for assay positive episodes, 13072 for assay negative episodes.

TABLE 6

CORRELATION OF IMMUNOBEAD AND RAGT RESULTS WITH TRANSFUSION OUTCOME

| | Assay Positive | | Assay Negative | |
|---|---|---|---|---|
| | CCI < 7500 | CC > 7500 | CCI < 7500 | CCI > 7500 |
| Immunobead | 16/18 (88.9%) | 2/18 (11.1%) | 4/33 (12.1%) | 29/33 (87.9%) |
| RAFT | 15/21 (71.4%) | 6/21 (28.6%) | 5/30 (16.7%) | 25/30 (83.3%) |

Twenty one episodes were RAGT positive; 15/21 (71.4%) had an unsuccessful outcome. Of the 30 RAGT negative episodes, 25/30 (83.3%) had a successful outcome. The mean 1 hour CCI was 3897 for RAGT positive episodes, 11118 for RAGT negative episodes.

In a single instance (involving patient 1), a donor initially associated with a positive immunobead assay and an unsuccessful outcome gave a negative assay and a successful outcome 1 month later. The initial transfusion was given just prior to preparation for BMT with high-dose cyclophosphamide and total nodal irradiation, suggesting that the alloantibody-producing lymphocytes were ablated, followed by disappearance of preformed antibody.

A plot of TCR vs. 1 hour CCI results from this study demonstrates the definition between positive and negative results, with no intervening area where CCI is proportional to TCR.

(iv) Misclassified Transfusion Episodes

Of the 6 episodes misclassified by the immunobead assay, only 1 (the case associated with granulocyte transfusion) was correctly classified by the RAGT. Six of the 11 episodes misclassified by the RAGT were correctly classified by the immunobead assay. In 5 instances, both tests gave misleading results.

In the first immunobead-assay-positive/successful-outcome episode (patient 1), the TCR was 5.3 and the 1 hour CCI 16,897. The 6 hour post platelet count had fallen to below the pre-transfusion level. The second case (patient 6) had a TCR of 253.7 (the 2nd highest recorded during the study), a 1 hour CCI of 10806 and a 16 hour CCI of 1965. When the same donor was used again 4 weeks later, the TCR was 183 and the 8 hour CCI 0. Both patients had unsuccessful outcomes with other donors associated with a positive immunobead assay.

The 4 assay-negative/unsuccessful-outcome cases were all associated with potential non-alloantibody-related causes of poor platelet survival. The first (patient 2) was associated with fever and occurred 5 days before the patient became refractory to all donors and was dropped from the study (see Patient and Donor Population section). The other 3 involved patient 1: the first occurred when platelets were given simultaneously with a granulocyte transfusion associated febrile reaction, and the other 2 after the patient had been incubated for ARDS but before he became refractory to all donors.

(v) Feasibility of Using Stored Platelets

The mean positive control/negative control ratios for both platelet donors at each time interval are displayed in Table 7. The results indicate some deterioration in antigenic integrity or availability between 1 and 5 days, following which no further major deterioration was detectable through the longest interval tested (60 days). Platelets stored in suspension at 4° C. maintained antigenic integrity slightly better than frozen platelets, although the difference was not marked. Although the positive controls used here remained markedly positive throughout the study, it is conceivable that plasmas with lower titers of anti-HLA antibody might become negative when tested against stored platelets. There was no significant loss of platelets due to storage during the study period.

TABLE 7

IMMUNOBEAD ASSAY RESULTS USING PLATELETS STORED FROZEN IN-LIQUID NITROGEN AND IN SUSPENSION AT 4° C.

| Storage Method | Day of Storage | | | | |
|---|---|---|---|---|---|
| | 1 | 6 | 15 | 30 | 40 |
| Platelet Donor #1 | | | | | |
| 4° C. | 53.8* | 26.7 | 23.9 | 25.7 | 21.0 |
| liquid N$_2$ | 32.6 | 20.7 | 23.9 | 25.3 | 10.5 |
| Platelet Donor #2 | | | | | |
| 4° C. | 103.0 | 33.5 | 49.3 | 53.1 | 48.6 |
| liquid N$_2$ | 71.5 | 30.6 | 35.6 | 40.5 | 32.0 |

*Data presented as mean positive control/negative control ratios.

H. Discussion of Transfusion Study Results

In this study, the immunobead assay was adapted to characterize anti-platelet alloantibodies to Class I HLA antigens and the results were applied to the problem of platelet crossmatching. The results indicate the test has sufficient predictive value to warrant wider scale application as a predictor of platelet transfusion success. Ideally, prospective donors would have platelets stored when they enter the donor pool. When a patient with a poor response to random donor platelets is encountered, his or her plasma could be assayed against a small panel of normal platelets chosen to represent the common HLA antigens. If negative, it could be assumed a problem other than alloimmunization against HLA antigens exists, and the expense of single donor platelets avoided. If positive, HLA matched platelets would be indicated. In the majority of cases where these are not available, the best matches could be pulled from the donor pool and their stored platelets tested, selecting those who test negative. Although our storage study extended only 60 days, other studies suggest much longer storage periods are feasible.

One potential drawback to the immunobead assay is its HLA specificity. Many authors have suggested that alloantibodies to platelet-specific antigens account for some percentage of transfusion failures, usually based on poor response to HLA identical platelets and/or the lack of demonstrable lymphocytotoxic antibody. However, alloantibodies to platelet-specific antigens have been difficult to demonstrate conclusively in this setting, and their true significance remains uncertain. Herman et al. used Western blots to study 7 patients refractory to HLA matched platelets, and were unable to demonstrate antibody to platelet specific antigen on the glycoprotein IIb/IIIa molecule. They concluded that antibodies to platelet-specific antigens are not commonly present. Our finding of only 1/51 instances of poor transfusion outcome where the RAGT was positive and the immunobead assay negative tends to support this. It seems more likely that unrecognized non-immunologic factors account for many if not all of these cases. However, it would seem prudent at present to use the RAGT or a similar non-HLA specific assay to evaluate the presence of antibody to other platelet-associated antigens in cases where the HLA-specific immunobead assay is negative in the face of poor platelet survival.

The foregoing is intended as illustrative of the present invention but not limiting. Numerous variations and modifications may be effected without departing from the true spirit and scope of the invention.

What is claimed is:

1. A method of assaying platelet compatibility between donor and patient comprising the steps of:
   (a) admixing an aliquot of serum of plasma from a patient with platelets of a prospective donor to form an aqueous, liquid admixture,
   (b) maintaining said admixture under biological assay conditions for a predetermined time period sufficient for any alloantibodies present in the serum or plasma to immunoreact with a platelet antigen to form a platelet antigen-alloantibody immunocomplex,
   (c) lysing the platelets of said admixture to form cellular debris and solubilize and platelet antigen-alloantibody immunocomplex, when said alloantibodies and said platelet antigen were present in said admixture,
   (d) separating the cellular debris from any solubilized immunocomplex formed in step (c),
   (e) affixing any of said separated, solubilized immunocomplex of step (d) present to a solid phase support capable of specifically binding said solubilized immunocomplex to form a solid phase-affixed platelet antigen-alloantibody immunocomplex, and
   (f) thereafter, assaying for the presence of said platelet antigen-alloantibody immunocomplex as a solid phase-affixed immunocomplex by reacting the immunocomplex present with a labeled specific binding agent that specifically binds to the immunocomplex, whereby the absence of immunocomplex indicates compatibility and the presence of immunocomplex indicates incompatibility of said donor and patient.

2. A method of typing cells for the presence of at least one of a group of cell surface antigens comprising the steps of:
   (a) reacting an aliquot of a cell sample to be typed with antibodies that react with an antigen epitope common to substantially all of the group of the cell surface antigens sought to form a common epitope-antibody immunocomplex,
   (b) lysing the cells of said sample to provide cellular debris and a solubilized common epitope-antibody immunocomplex,
   (c) separating the cellular debris from said solubilized immunocomplex formed in step (b),
   (d) affixing said immunocomplex to a solid phase support capable of specifically binding said immunocomplex to form a solid phase-affixed immunocomplex,
   (e) reacting the solid phase-affixed immunocomplex with labeled paratopic molecules that immunoreact with at least one specific cell surface antigen epitope of the group of cell surface antigens to form a second solid phase-affixed immunocomplex, and
   (f) assaying for the presence of said labeled paratopic molecules in said solid phase-affixed second immunocomplex, and thereby for the presence of said at least one specific cell surface antigen epitope.

3. The method of claim 2 wherein said label comprises a radiolabeling agent.

4. The method of claim 2 wherein said group of cell surface antigens comprises the HLA antigens.

5. The method of claim 2 wherein said separated solubilized common epitope-antibody complex is divided into a plurality of aliquots, said aliquots are individually reacted with members of a panel of labeled paratopic molecules, and each of said aliquots is then assayed for the presence of a second immunocomplex.

6. The method of claim 5 wherein said at least one specific cell surface antigen epitope is an epitope of an HLA antigen.

* * * * *

UNITED STATES PATENT AND TRADEMARK OFFICE
CERTIFICATE OF CORRECTION

| | |
|---|---|
| PATENT NO. | : 5,336,597 |
| DATED | : August 9, 1994 |
| INVENTOR(S) | : Robert McMillan |

It is certified that error appears in the above-identified patent and that said Letters Patent is hereby corrected as shown below:

<u>Column 1,</u>
Line 4, insert:

-- This invention was made with government support under Grant No. AM 16125 from the National Institutes of Health. The U.S. government may have certain rights in the invention. --

Signed and Sealed this

Fourth Day of June, 2002

*Attest:*

*Attesting Officer*

JAMES E. ROGAN
*Director of the United States Patent and Trademark Office*